United States Patent [19]

Slaugh

[11] Patent Number: 5,068,488

[45] Date of Patent: Nov. 26, 1991

[54] OLEFIN ETHYLATION PROCESS

[75] Inventor: Lynn H. Slaugh, Cypress, Tex.

[73] Assignee: Shell Oil Company, Houston, Tex.

[21] Appl. No.: 517,772

[22] Filed: May 2, 1990

[51] Int. Cl.$^5$ ............................................. C07C 2/24
[52] U.S. Cl. .................................. 585/516; 585/533
[58] Field of Search .................................. 585/516, 533

[56] References Cited

U.S. PATENT DOCUMENTS

| | | | |
|---|---|---|---|
| 2,492,693 | 12/1949 | Freed | 260/683.15 |
| 3,175,020 | 3/1965 | Wilkes | 260/683.15 |
| 3,651,161 | 3/1972 | Waragai et al. | 260/671 C |
| 3,676,523 | 7/1972 | Mason | 260/683.15 D |
| 3,686,351 | 8/1972 | Mason | 260/683.15 D |
| 3,737,475 | 6/1973 | Mason | 260/683.15 D |
| 3,825,615 | 7/1974 | Lutz | 260/683.15 D |
| 4,020,121 | 4/1977 | Kister | 260/683.15 D |
| 4,375,571 | 3/1983 | Hart et al. | 585/431 |
| 4,433,981 | 2/1984 | Slaugh et al. | 55/59 |
| 4,505,787 | 3/1985 | Fuller et al. | 204/67 |
| 4,511,748 | 4/1985 | Kudoh et al. | 585/467 |
| 4,544,790 | 10/1985 | Drake | 585/516 |
| 4,595,787 | 6/1986 | Drake | 585/516 |
| 4,609,637 | 9/1986 | Drake | 502/174 |
| 4,661,466 | 4/1987 | Drake et al. | 502/184 |
| 4,988,658 | 1/1991 | Drake | 585/516 |

OTHER PUBLICATIONS

Pines et al., "Sodium Catalyzed Reactions. II. Side-Chain Ethylation of Alkyl Aromatic Hydrocarbons Catalyzed by Sodium", J. of American Chemical Society, vol. 77, pp. 554–559, 1955.

Primary Examiner—Curtis R. Davis
Attorney, Agent, or Firm—Pamela J. McCollough

[57] ABSTRACT

A process for ethylating detergent-range olefins which comprises contacting a detergent-range olefin with ethylene in the presence of a catalyst prepared by impregnating a porous alumina support with a metal compound decomposable to an oxide upon calcination wherein said metal is selected from the group consisting of potassium, rubidium, cesium and mixtures thereof, and subsequently calcining the resulting material at a temperature of from about 450° C. to about 750° C.

13 Claims, No Drawings

5,068,488

OLEFIN ETHYLATION PROCESS

FIELD OF THE INVENTION

This invention relates to a process for the ethylation of detergent-range olefins with a catalyst prepared by impregnating a porous alumina support with a metal compound decomposable to an oxide upon calcination wherein said metal is selected from the group consisting of potassium, rubidium, cesium and mixtures thereof, and subsequently calcining.

BACKGROUND OF THE INVENTION

Various processes for the alkylation of olefins employing alkali metal catalysts alone or supported on suitable carriers, together with certain promoters have previously been reported. U.S. Pat. No. 2,492,693 discloses the use of an alkali metal (sodium) catalyst and a polynuclear aromatic hydrocarbon promoter for the intermolecular condensation of different monoolefins. In the *Journal of American Society*, vol. 77, pp. 554–559 (1955), the reaction of alkyl aromatic compounds with ethylene takes place in the presence of a sodium catalyst and an organic compound promoter. British Patent No. 2,269,280 discloses alkylating an aromatic hydrocarbon with a monoolefin in the presence of a catalyst prepared by dispersing an alkali metal on a potassium compound. U.S. Pat. No. 4,511,748 discloses a process for alkylating aromatic hydrocarbons with olefins using a catalyst comprising sodium and/or sodium amide on a potassium carbonate carrier.

Other known process for the dimerization of olefins employing potassium as catalyst component are found in U.S. Pat. No. 3,175,020, which discloses catalysts having potassium metal on an alumina carrier; and U.S. Pat. Nos. 4,609,637, 4,661, 466, 4,544, 790 and 4,505,787 which teach the use of elemental alkali metals deposited on potassium carbonate catalyst supports.

U.S. Pat. No. 3,651,161 discloses a process for the alkylation of compounds with an active hydrogen, allylic or benzylic, with the use of sodium/pyrene charge transfer complex, or a potassium/biphenyl charge transfer complex.

It has now been found that a catalyst comprising a metal compound decomposable to an oxide upon calcination wherein said metal is selected from the group consisting of potassium, rubidium, cesium and mixtures thereof, supported on a porous alumina support, when properly activated, promotes an ethylation reaction in which ethylene is added to detergent-range olefins to produce more-branched olefins of higher molecular weight.

SUMMARY OF THE INVENTION

The present invention provides a process for the ethylation of detergent-range olefins to produce higher molecular weight olefins which comprises reacting ethylene with a detergent-range olefin in the presence of a catalyst prepared by impregnating a porous alumina support with a metal compound decomposable to an oxide upon calcination wherein said metal is selected from the group consisting of potassium, rubidium, cesium and mixtures thereof and subsequently calcining the resulting material at a temperature of from about 450° C. to about 750° C.

DESCRIPTION OF THE PREFERRED EMBODIMENTS

The present invention relates to a process for ethylating detergent range olefins by contacting a detergent-range olefin with ethylene in the presence of a catalyst prepared by impregnating a porous alumina support with a metal compound decomposable to an oxide upon calcination wherein said metal is selected from the group consisting of potassium, rubidium, cesium and mixtures thereof, and subsequently calcining the resulting material at a temperature of from about 450° C to about 750° C. The detergent range olefins are ethylated in the instant invention to prepare more-branched olefins having higher molecular weights. As used herein, "ethylation" and "ethylating" refer to the addition of one or more ethyl moieties ($CH_3Ch_2-$) to an organic substrate which in the instant specification is an olefin. In a preferred embodiment, straight-chain olefins can be converted to mono-branched olefins having an ethyl group pendant to the main chain, or if desired, multi-branched products can be obtained.

The detergent range olefins suitable for use in the present invention are olefins having from about 8 to about 22 carbon atoms, preferably from about 8 carbon atoms to about 18 carbon atoms. These olefins can be alpha olefins or internal olefins and they may be linear or branched. Single cut olefins or mixtures of olefins may also be used. In a particularly preferred embodiment, the olefin contains from about 12 to about 18 carbon atoms.

Preferred for use as olefin reactant for the practical reason of availability are the commercial olefin products in the $C_8$ to $C_{22}$ range. One such example of such olefins is the Chevron Alpha Olefin product series (trademark of and sold by Chevron Chemical Co.), manufactured by the cracking of paraffin wax Commercial production is more commonly accomplished by the oligomerization of ethylene using procedures well known in the art. The resulting oligomerization products are substantially of linear structure and thus products are substantially of linear structure. Commercial olefin products manufactured by ethylene oligomerization are marketed in the United States by Shell Chemical Company under the trademark Neodene and by Ethyl Corporation as Ethyl Alpha-Olefins. Specific procedures for preparing suitable linear olefins from ethylene are described in U.S. Pat. Nos. 3,676,523, 3,686, 351, 3,737,475, 3,825,615 and 4,020,121. While most of such olefin products are comprised largely of alpha-olefins, higher linear internal olefins ar also commercially produced, for example, by the chlorination-dehydrochlorination of paraffins, by paraffin dehydrogenation and by isomerization of alpha-olefins. Linear internal olefin products in the $C_8$ to $C_{22}$ range are marketed by Shell Chemical Company and by Liquichemica Company. These commercial products, whether predominantly internal or alpha-olefins typically contain about 70 percent by weight or more, most often about 80 percent by weight or more, linear monoolefins in a specified carbon number range (e.g., $C_1O$ fo $C_{12}$ $C_{11}$ to $C_{15}$, $C_{12}$ to $C_{13}$, $C_{15}$ to $C_{18}$ etc.), the remainder of the product being olefin of other carbon number or carbon structure, diolefins, paraffins, aromatics and other impurities resulting from the synthesis process. $C_8$ to $C_{14}$ olefins are considered the most preferred olefins for use in the instant invention.

The catalysts utilized for the reaction of ethylene with a detergent-range olefin in the instant invention are prepared for example, by impregnating or otherwise providing a porous alumina support with an alkali metal compound decomposable upon calcination to the oxide wherein the metal compound is selected from the group consisting of potassium rubidium, cesium and mixtures thereof and then calcining the resultant composition at a temperature ranging from about 450° C. to about 750° C., preferably from about 500° C. to about 700° C. Calcining below the desired lower temperature limits results in catalysts which are not active, and calcining above the desired upper temperature limits results in excessive sintering with a resultant degradation of catalyst properties. It is thought that the decomposable compound(s) during the calcination react after intermediate oxide formation with the alumina to form a metal aluminate. Suitable impregnating alkali metal compounds that decompose during calcination include, for example, carbonates, bicarbonates hydroxides, chelates, alkoxylates and salts of other weak acids or salts of strong acids that decompose upon calcination such as the nitrates.

The calcination is carried out in any atmosphere: vacuum, reducing, inert or oxidizing, with reducing and inert atmospheres being preferred. When the decomposable compound has an organic anionic moiety such as carboxylate, alkoxylate chelate, etc., it is preferred to carry out the calcination in a reducing atmosphere such as hydrogen or an inert atmosphere such as nitrogen. Calcination times are not critical and depend on calcining temperatures, higher temperatures requiring shorter times and vice versa. Typical times range from about 0.1 to about 50 hours. The time-temperature combination selected should be such that the metal oxide or decomposable compound carbonate reacts almost completely with the alumina. In a preferred embodiment, the catalyst is calcined in air and thereafter activated by flowing nitrogen over the catalyst at elevated temperatures, about 575° C., for about sixteen hours.

The alkali metals used to form the catalyst of the invention are potassium, rubidium and cesium. Combinations of these metals can also be utilized. Preferred impregnating materials for the alumina are potassium carbonates, potassium carboxylates and potassium nitrate. Salts of strong acids that do not completely decompose such as, for instance, sulfates and halides are not satisfactory.

The alumina employed in the catalyst can be any of the variety of available aluminas or alumina hydrates, such as alumina gel, activated alumina, gamma alumina and the like. The most suitable aluminas for use in the present invention are found to be those having surface areas ranging from about 1 $m^2/g$ to about 500 $m^2/g$, preferably from about 50 $m^2/g$ to about 400 $m^2/g$. In a preferred embodiment, the alumina support is gamma alumina. Aluminas are readily available commercially which are suitable for use in the instant invention. The following table lists several commercial gamma aluminas and their properties which are suitable.

| Alumina | Surface Area, $m^2/g$ | Pore Vol. Co/gm | Na ppm | $SO_4$ % wt. | $Fe_2O_3$ % wt. | Cl— % wt. |
|---|---|---|---|---|---|---|
| CCI (a) | 252 | 0.8 | 160 | 0.06 | — | 0.02 |
| KA-201 (b) | 365 | 0.42 | 600 | 0.03 | — | 0.01 |
| RA-1 (c) | 263 | 0.26 | 4700 | 0.02 | 0.18 | — |
| ACCP (d) | 225 | 0.68 | 580 | 0.6 | — | 0.6 |
| Norton | 218 | 0.62 | 0.51 | 0.03 | — | 0.03 |
| CATAPAL (e) | 348 | 0.91 | | | | |
| FILTROL (f) | 214 | 0.82 | | | | |

(a) Catalysts & Chemicals, Inc., now United Catalysts
(b) Kaiser
(c) Reynolds Corp.
(d) American Cyanamid Corp.
(e) Conoco Corp.
(f) Filtrol Corp.

Any conventional methods known for adding the metal oxide or decomposable compound to the alumina can be employed. A preferred method is to soak the alumina support pellets in an aqueous solution of the decomposable metal compound(s), dry the impregnated alumina and then calcine at temperatures in the range of from about 450° C. to about 750° C., preferably from about 500° C. to about 700° C. Dry mixing can also be used. Since the metal oxide or decomposable compound is primarily reacting with the surface alumina, both external and internal pore surface, then the maximum amount of impregnating compound that can be effectively utilized will depend on the surface area. Ordinarily, the molar ratio of metal added to alumina will range from about 2:1 to about 1:50, preferably from about 1:1 to about 1:25. Preferably, the weight of the metal oxide or decomposable compound added will range from about 0.1 percent by weight to about 30 percent by weight, more preferably from about 1 percent by weight to about 25 percent by weight, and most preferably, from about 5 percent by weight to about 20 percent by weight measured as the metal. In a preferred embodiment, a given portion of alumina pellets is impregnated with just enough aqueous solution of decomposable metal to fill the pore volume of the alumina, then dried at temperatures of up to about 125° C., and then calcined at temperatures in the range of from about 450° C. to about 750° C., preferably from about 500° C. to about 700° C.

The process of the instant invention can be carried out using either batch or continuous types of operation, although the catalysts of the instant invention are particularly well suited for continuous or fixed bed operation. Suitable equipment such as, for example, autoclaves, tubular reactors and the like can be employed. Materials such as steel, stainless steel, glass-lined reactors and the like can be employed.

The reaction temperatures and pressures can vary depending on the olefin feed employed and the products desired. Typically, a temperature in the range of from about 150° C. to about 400° C. and a pressure in the range of from about 200 psig to about 3000 psig is suitable. The temperature is preferably in the range of from about 150° C. to about 300° C., and more preferably in the range of from about 200° C. to about 250° C. The pressure is preferably in the range of from about 500 psig to about 2000 psig, and more preferably in the range of from about 800 psig to about 1200 psig. As the reaction temperatures and pressures are lowered, the conversion is lowered. If, for example, a monoethylated olefin is desired, it will be necessary to limit the feed conversion by lowering the temperature and pressure as the initial monoethylated olefin can undergo further ethylation. Temperatures in the range of from about 150° C. to about 250° C. and pressures in the range of from about 800 psig to about 1200 psig are most preferred as they result in a minimal amount of by-products from side reactions such a dimerization and polymerization.

The ethylation reaction is usually carried out in a liquid phase and if desired, solvents or diluents for the reactants can be used. Suitable diluents include saturated aliphatic hydrocarbons, e.g., pentane, hexane, cyclohexane; and aromatic compounds such as benzene and toluene.

The contact time required for the ethylation reaction depends upon several factors such as temperature, pressure, the level of conversion desired and the like. The length of time during which the ethylene and the detergent-range olefin are contacted with the catalyst are usually between about one hour and about twenty hours, although shorter and longer contact times can be utilized. Preferably, the contact times are in the range of from about two hours to about ten hours. When the reaction is carried out in continuous fashion, the reactant/catalyst contact time may be expressed in terms of the liquid hourly space velocity (volume of reactants per volume of catalyst per hour, LHSV). The LHSV is suitably in the range of from about 0.1 to about 5.0, preferably from about 0.5 to about 1.0 LHSV.

The relative amounts of olefin reactant and ethylene are such that an ethylation product is produced which has the desired degree of branching in the carbon chain. In general, the olefin is contacted with sufficient ethylene for a sufficient time to yield a mixture of ethylated olefins characterized as the addition product of an average of between about 1.0 and 1.3 mols of ethylene per mole of olefin. Addition of greater amounts of olefin results in a larger portion of more-branched products. An excess of olefin reactant results in the production of ethylated olefins having primarily one added ethyl branch in the molecule. Preferably, the olefin reactant is used in such an excess that of the olefin reactant molecules, no more than about 50%, preferably no more than about 20%, and more preferably, no more than about 15% react with two or more ethylene molecules to yield ethylated olefins having more than one added ethyl branch and/or an added branch of more than 2 carbon atoms. Maintaining a relatively low conversion, e.g., 10-20%, of olefin reactant during ethylation also aids in preventing the formation of polyethylated products.

The more-branched, higher molecular weight olefin products prepared according to the present process are useful in a wide variety of applications such as, for example, making a broad range of surfactants, including nonionic, anionic, cationic and amphoteric surfactants. The olefin products prepared according to the instant invention are particularly useful for making surfactant materials which have superior cold water detergency and better handling characteristics than their linear counterparts.

The ranges and limitations provided in the instant specification and claims are those which are believed to particularly point out and distinctly claim the present invention. It is, however, understood that other ranges and limitations which perform substantially the same function in substantially the same way to obtain the same or substantially the same result are intended to be within the scope of the instant invention as defined by the instant specification and claims.

The instant invention is illustrated by the following examples which are provided as illustration and are not to be construed as limiting the invention.

ILLUSTRATIVE EMBODIMENTS

Catalyst Preparation

The following example illustrates the preparation of the catalysts of the present invention.

15 Grams of anhydrous $K_2CO_3$ were dissolved in 45 milliliters of deionized water. This solution was poured on 85 grams of Kaiser grade A-210 alumina (14-30 mesh) while the latter is being stirred. The volume of the solution and the weight of the alumina was proportioned to essentially fill the pores in the alumina without excess solution remaining after impregnation. The impregnated material was dried at 100° C for 18 hours in air. The dried material was then calcined in a tube of flowing nitrogen for 16 hours at 575° C. Analysis indicated that the composition contained about 9.3 percent by weight of potassium measured as the potassium metal.

Similar catalysts are prepared, for example by using solutions of potassium nitrate, potassium bicarbonate, potassium acetate and potassium nitrate.

ETHYLATION PROCESS

These examples illustrate the use of potassium carbonate/alumina catalysts in a series of ethylation reactions in which a detergent-range olefin, 1-dodecene was contacted and reacted with ethylene to produce more-branched higher molecular weight olefins.

In Example 1, 25 grams of 1-dodecene was charged to a one-liter autoclave, under nitrogen blanket, together with 6 grams of the potassium carbonate/alumina catalyst prepared as described above. After thoroughly flushing with nitrogen and evacuating, the autoclave was charged with 800 psig ethylene. The autoclave contents were then heated under stirring to about 151° C. As the ethylation reaction commenced, ethylene was added to maintain a total pressure in the range of from about 500 -800 psig. After about 5 hours, the reaction was terminated and the autoclave contents were allowed to cool to room temperature. A total of 31 grams of reactants and catalyst were removed and then filtered to separate catalyst. The results are presented in Table I.

For Example 2, the ethylation of 1-dodecene was carried out according to the same procedures, and using the same quantities of catalyst and olefin reactant, as described for Example 1. The results are presented in Table I For Example 3, the ethylation of 1-dodecene was carried out according to the same procedures, and using the same quantities of catalyst and olefin reactant, as described for Example 1. The results are presented in Table I For Example 4, the ethylation of 1-dodecene was carried out according to the same procedures, and using the same quantities of catalyst and olefin reactant, as described for Example 1. The results are presented in Table I

TABLE I

ETHYLATION OF 1-DODECENE

| | Time (Hrs.) | Press. (psig) | Temp. (°C.) | LHSV (equiv) | 1-Dodecene Conv., % | Selectivity, Mole % | | |
|---|---|---|---|---|---|---|---|---|
| | | | | | | $C_{14}H_{28}$ | $C_{16}H_{32}$ | $C_{18}H_{36}$ |
| Example 1 | 5 | 800 | 151 | 1.0 | 6.7 | 98.6 | 1.4 | 0 |
| Example 2 | 5 | 800 | 175 | 1.0 | 13.1 | 98.4 | 1.6 | 0 |
| Example 3 | 5 | 800 | 201 | 1.0 | 28.6 | 89.2 | 10.4 | 0.4 |
| Example 4 | 5 | 800 | 252 | 1.0 | 46.4 | 77.8 | 20.5 | 1.7 |

As can be seen in Table I, relatively low conversions result in primarily mono-ethylated product. It can also be seen that deeper conversions result in an increase in branching.

What is claimed is:

1. A process for ethylating detergent range olefins which comprises contacting a detergent-range olefin with ethylene in the presence of a catalyst prepared by impregnating a porous alumina support with a metal compound decomposable to an oxide upon calcination wherein said metal is selected from the group consisting of potassium, rubidium, cesium and mixtures thereof, and subsequently calcining the resulting material at a temperature of from about 450° C to about 750° C.

2. The process of claim 1 wherein the catalyst is calcined at a temperature ranging from about 500° C to about 700° C.

3. The process of claims 1 or 2 wherein said catalyst is calcined in an inert atmosphere.

4. The process of claims 1 or 2 wherein said catalyst is calcined in a reducing atmosphere.

5. The process of claim 1 or 2 wherein the metal compound added to the alumina support ranges from about 0.1 to about 30 percent by weight measured as the metal.

6. The process of claim 1 or 2 wherein the metal compound added to the alumina support ranges from about 1 to about 25 percent by weight measured as the metal.

7. The process of claim 1 or 2 wherein the metal compound added to the alumina support ranges from about 5 to about 20 percent by weight measured as the metal.

8. The process of claim 1 or 2 wherein the metal compound added to the alumina support is selected from the group consisting of potassium carbonates, potassium carboxylates, potassium nitrate and mixtures thereof.

9. The process of claim 8 wherein the metal compound added to the alumina support is potassium carbonate.

10. The process of claim 1 wherein said detergent-range olefin is an olefin having from about 8 to about 22 carbon atoms.

11. The process of claim IO wherein said detergent-range olefin is an olefin having from about 8 to about 18 carbon atoms.

12. The process of claim 1 wherein said ethylation is carried out at a temperature in the range of from about 150° C. to about 400° C. and a pressure in the range of from about 200 psig to about 3000 psig.

13. The process of claim 12 wherein said ethylation is carried out at a temperature in the range of from about 150° C. to about 300° C. and a pressure in the range of from about 500 psig to about 2000 psig.

* * * * *